United States Patent [19]
Baier et al.

[11] Patent Number: 5,729,470
[45] Date of Patent: Mar. 17, 1998

[54] SYSTEM FOR CONTINUOUS IN-SITU MEASUREMENT OF CARBON IN FLY ASH

[75] Inventors: Gunar Baier, Mannheim; Armin Gasch, Heidelberg; Dietmar Treibert, Heddesheim, all of Germany; Juris G. Labrencis, Vernon, Conn.; James M. Niziolek, Enfield, Conn.; Joseph W. Quinn, Bloomfield, Conn.

[73] Assignee: Combustion Engineering, Inc., Windsor, Conn.

[21] Appl. No.: 641,663

[22] Filed: May 1, 1996

[51] Int. Cl.[6] .................................................. G01N 22/00
[52] U.S. Cl. .................... 364/497; 324/633; 324/636; 324/637; 431/76; 73/23.31; 73/23.33; 73/28.01
[58] Field of Search .................... 364/497; 73/23.31, 73/23.33, 28.01; 431/75, 76; 422/94; 356/436, 437, 438, 439; 250/338.5, 339.05, 339.06, 339.09, 343; 374/122

[56] References Cited

U.S. PATENT DOCUMENTS

5,155,047 10/1992 Cioni et al. ............................ 436/139
5,177,444 1/1993 Cutmore ................................ 324/637

Primary Examiner—Emanuel T. Voeltz
Assistant Examiner—Tony M. Cole
Attorney, Agent, or Firm—Arthur E. Fournier, Jr.

[57] ABSTRACT

A system including a resonant cavity for measuring in-situ and in real time the Carbon content of the fly ash produced from the combustion process occurring within a pulverized coal-fired steam generator. The resonant cavity basically includes an intelligence section, a transmitting section, a cavity section and a receiving section. When the system including the resonant cavity is so employed the measurements gained therefrom may be utilized either by an operator or as input to a boiler control system or both in order that corrective action may be implemented when such is required.

15 Claims, 8 Drawing Sheets

SYSTEM FOR CONTINUOUS IN-SITU MEASUREMENT OF CARBON IN FLY ASH

BACKGROUND OF THE INVENTION

This invention relates to a system operable for purposes of making continuous, in-situ measurements of the Carbon content of the fly ash produced from the combustion process occurring within the furnace of a pulverized coal-fired steam generating power plant, and, more specifically, to such a system wherein a resonant cavity is utilized for such purposes. As will be described more fully herein subsequently, the Carbon content in the fly ash can be determined from its effect on key parameters of the resonant cavity such as the cavity's resonant frequencies, $f_q$, the transmitted intensity, I, at resonance and the cavity's full width at half maximum (FWHM) frequency difference, BW.

Fly ash is the combination of inert and inorganic residue resulting from the incomplete combustion of pulverized coal. The pulverized coal contains varying amounts of carbon or coke particles. In general, the inorganic ash particles consist primarily of silicates, oxides and sulfates, together with small quantities of phosphates and other trace compounds. Particle size varies from below 0.01 micrometers to over 100 micrometers in diameter.

The presence of unburned Carbon in boiler fly ash has important economic and environmental consequences to the operator of a coal-fired boiler installation. Its presence is a measure of inefficient fuel utilization which means that more fuel must be burned in order to obtain a given output and which in turn directly increases the cost of electrical power generation. Furthermore, inefficient fuel utilization by virtue of requiring more fuel to be burned in order to produce a given output increases the presence of $NO_x$ emissions which is the basis for environmental concerns. Thus, knowledge of the Carbon content of boiler fly ash is an important element in establishing a low $NO_x$ boiler emission strategy. In addition, low Carbon fly ash can be a potential source of income to the operator of a pulverized coal-fired boiler in that fly ash can be employed as a building material if the Carbon content in the fly ash is sufficiently low. Fly ash with a high Carbon content is unsuitable as a building material and normally requires the use of expensive waste disposal methods.

Typical of current methods for determining the Carbon content of boiler fly ash is that which consists of inserting an extraction probe into the combustion exhaust gas stream and capturing a predetermined amount of fly ash. Carbon content can then be analyzed by one of two methods. In accordance with one of such methods, first the fly ash sample is placed in a network analyzer. From this arrangement, scattering matrix parameters, $S_{jk}(\omega)$, are measured from which a reflection coefficient, R, and a transmission coefficient, T, are calculated. Based upon these calculations complex permittivity, $\epsilon_r$, and permeability, $\mu r$, are in turn calculated and compared with tabulated values. In accordance with the second of such methods, the fly ash sample is placed in an oven and burned at a specified temperature for a specified time. By comparing the initial mass of the sample with the mass of that which remains after burning, the mass of the Carbon in the fly ash sample can be calculated. Alternatively, the byproducts of the burning can be analyzed for their carbon monoxide, CO, or carbon dioxide, $CO_2$, content to give a measure of the Carbon content in the fly ash sample.

However, current methods for measuring the Carbon content in boiler fly ash are deficient in several regards. First, these methods are typically extractive in nature in that a specified quantity of fly ash must be captured in order to analyze its Carbon content. This is a time consuming process which yields a sample that is representative of only one location within the flue gas stream. In fact, unknown temperature gradients across the flue gas stream will cause concomitant gradients in the Carbon content of the fly ash. Furthermore, these methods require the expense associated with employing additional analytic equipment and entail a lengthy time delay between sampling and final analysis of Carbon content. As a consequence of the time required in sampling and the further delay in analyzing the sample, current methods are largely ineffective as a means of optimizing in real time fuel utilization or in the control in real time of $NO_x$ emissions, because of the time it takes to initiate corrective action.

The new method, in accordance with the present invention, for measuring the Carbon content of boiler fly ash addresses these deficiencies through the use of a resonant cavity that provides in-situ, real time measurements without exotic or expensive components. Since the new method of the present invention makes measurements in real time, these measurements are ideally suited for use as a feedback signal in a boiler control system seeking to optimize fuel utilization or reduce $NO_x$ emissions. In addition, since measurements are based upon a volume inspection and as such are representative of a volumetric average, they are less susceptible to the presence of gradients in the Carbon content in the boiler fly ash. Furthermore, due to the multiple reflections of the electromagnetic radiation within the resonant cavity, measurements are possible even in the presence of extremely dilute fly ash, i.e., relatively small amounts of fly ash present in the flue gas stream. Still further, measurement of the changes in any one of the three key resonant cavity parameters is capable of providing reliable measurements of the Carbon content within the boiler fly ash. Lastly, the three key resonant cavity parameters are more sensitive to changes in Carbon content in fly ash at the operating frequencies of the cavity than would be displayed at lower frequencies.

The simplest resonant cavity is the Fabry-Perot etalon as explained in chapter four of *Optical Electronics* by A. Yariv, 4th edition, Saunders College Publishing, 1991. This consists of two parallel, plane reflectors, or mirrors, located a fixed distance apart, between which there may exist a vacuum or some medium. Within the etalon, electromagnetic radiation, originating from an external source, is repeatedly reflected back and forth between the mirrors. At certain frequencies, $f_q$, of the electromagnetic radiation, resonance occurs within the cavity. This is marked by periodic sharp peaks in the intensity, I, of the radiation transmitted by the cavity.

A lossy resonant cavity is characterized by three measurable parameters of importance. First, the resonant frequencies, $f_q$, are those frequencies of the electromagnetic radiation at which resonance occurs. They are located at integer, m, multiples of the cavity's Free Spectral Range, FSR, and are given by $$FSR = m \frac{c}{2nL}$$

$$m = 1, 2, 3 \ldots$$

where c is the speed of light in vacuo, n is the refractive index of the medium between the mirrors and L is length between the mirrors. Secondly, the resonant peaks possess a full width at half maximum (FWHM) frequency difference, BW, which is given by $$BW = \frac{c}{2nL} \frac{1-(R_1 R_2)^{1/2}}{\pi (R_1 R_2)^{1/4}}$$

where $R_1$ and $R_2$ are the reflectances of the respective mirrors. Thirdly, the intensity, I, of the electromagnetic radiation transmitted by the etalon is given by $$I = \frac{I_o T_{max}}{1 + F \sin^2(\phi/2)}$$

where $I_o$ is the intensity of the incident beam, $T_{max}$ is the maximum transmission of the cavity, F is the coefficient of finesse and $\phi$ is the total phase change between two successive reflections within the cavity.

Typical of the uses of a resonant cavity are that of an optical spectrum analyzer or a laser resonator as further explained in chapters four and six of *Optical Electronics* by A. Yariv.

As a spectrum analyzer one mirror of the Fabry-Perot etalon is allowed to move along an axis perpendicular to the planes of the mirrors. As such, the etalon operates as a scanning interferometer wherein the spectral content of an input signal can be analyzed. As a laser oscillator the medium between the mirrors of a Fabry-Perot etalon consists of a gain medium possessing an atomic population inversion. As such, an incident optical signal undergoes amplification due to stimulated emission during its multiple passes within the etalon. The output signal is a laser beam.

A further example of a typical prior art use of a resonant cavity is that of optical bistable devices as explained in chapter twenty-one of *Fundamentals of Photonics* by B. Saleh and M. Teich, John Wiley and Sons, Inc., 1991. As such, the Fabry-Perot etalon acts as an optical switch capable of use, for instance, in binary logic and computation.

To improve the stability of a resonant cavity spherical mirrors may be used instead of plane mirrors. This confines the beam to the cavity and reduces the likelihood of the beam escaping through the sides of the cavity prematurely due to either a lack of perpendicularity between the beam and mirrors or due to a lack of parallelism between the mirrors.

Thus, it is sought to provide by way of the present invention a new and improved method for measuring the Carbon content in the fly ash produced from the combustion process occurring within the furnace of a steam generating power plant.

It is further sought to provide by way of the present invention such a new and improved method for measuring the Carbon content of boiler fly ash wherein measurements taken in accordance therewith are in situ.

It is also sought to provide by way of the present invention such a new and improved method for measuring the Carbon content of boiler fly ash wherein measurements taken in accordance therewith are made in real time.

In addition it is sought to provide by way of the present invention such a new and improved method for measuring the Carbon content of boiler fly ash wherein measurements taken in accordance therewith may be utilized in a boiler control system.

It is another object of the present invention to provide such a new and improved method for measuring the Carbon content in boiler fly ash that is virtually insusceptible to gradients in the boiler fly ash within the flue gas stream.

It is further sought to provide by way of the present invention such a new and improved method for measuring the Carbon content of boiler fly ash that is suitable for use in the harsh environment of a steam generating power plant.

It is still further sought to provide by way of the present invention such a new and improved method for measuring the Carbon content of boiler fly ash that is capable of providing accurate measurements even when very dilute concentrations of fly ash are present in the flue gas stream.

It is another object of the present invention to provide such a new and improved method for measuring the Carbon content in boiler fly ash that is flexible in nature in that measurements in the changes in only one of three key resonant cavity parameters can be used to acquire meaningful results.

SUMMARY OF THE INVENTION

In accordance with one aspect of the present invention there is provided a system, which makes use of a resonant cavity with attendant componentry, and which is operable for the purpose of making in-situ, real time measurements of the Carbon content in the fly ash that is produced from the combustion process occurring within the furnace of a pulverized coal-fired steam generating power plant. The subject resonant cavity and attendant componentry of the said system generally consist of an intelligence section, a transmitting section, a cavity section and a receiving section.

The intelligence section is designed so as to be operable to provide as output an electrical drive signal that acts as input to the transmitting section. The drive signal is a biased, periodic ramp voltage. The bias energizes an oscillator within the transmitting section which, without further stimulation, produces a constant amplitude, constant frequency sinusoidal signal of electromagnetic radiation. The ramp causes the oscillator signal to sweep through a predetermined frequency span which will encompass one or more cavity resonances. In addition, the intelligence section accepts as input a detected signal originating from the receiving section as well as a reference signal originating from the transmitting section. The detected signal is a DC voltage proportional to the power of the oscillator signal detected by the receiving section. The reference signal is also a DC voltage, but proportional to the power of a signal decoupled from and a small fraction of the oscillator signal. This will allow the intelligence section to compare the signal transmitted to the cavity with the signal received from the cavity and determine whether any degradation in the oscillator signal is due to the presence of Carbon in the boiler fly ash or due to normal variations in the oscillator signal. The intelligence section is further designed so as to be operable to provide as output a signal that is representative of the percent of Carbon in the fly ash and which may simply be displayed on an operator's monitor or act as input to a boiler control system or both in order that corrective action may be taken, if required.

As noted above the transmitting section accepts as input a drive signal originating from the intelligence section and provides as output a reference signal. The transmitting section is further designed so as to be operable to provide as output an oscillator signal of electromagnetic radiation. The oscillator signal is a constant amplitude sinusoidal signal that repeatedly sweeps through a predetermined frequency span and which acts as input to the cavity section.

The cavity section is designed so as to be operable to accept as input the oscillator signal originating from the transmitting section which, after repeated reflections within the cavity, is delivered to the receiving section. As the oscillator signal sweeps through a predetermined frequency span, resonance occurs within the cavity, as typified by sharp peaks in the transmission of signal power to the receiving section.

The receiving section is designed so as to be operable to accept as input the oscillator signal originating from the transmitting section and passing through the cavity section and to then provide as output the detected signal, mentioned above, which in turn acts as one input to the intelligence section.

In accordance with another aspect of the present invention there is provided a method utilizing a resonant cavity for measuring in-situ and in real time the Carbon content of the fly ash produced from the combustion occurring within a solid fuel-fired steam generator.

DESCRIPTION OF THE PREFERRED EMBODIMENT

Figure 1:
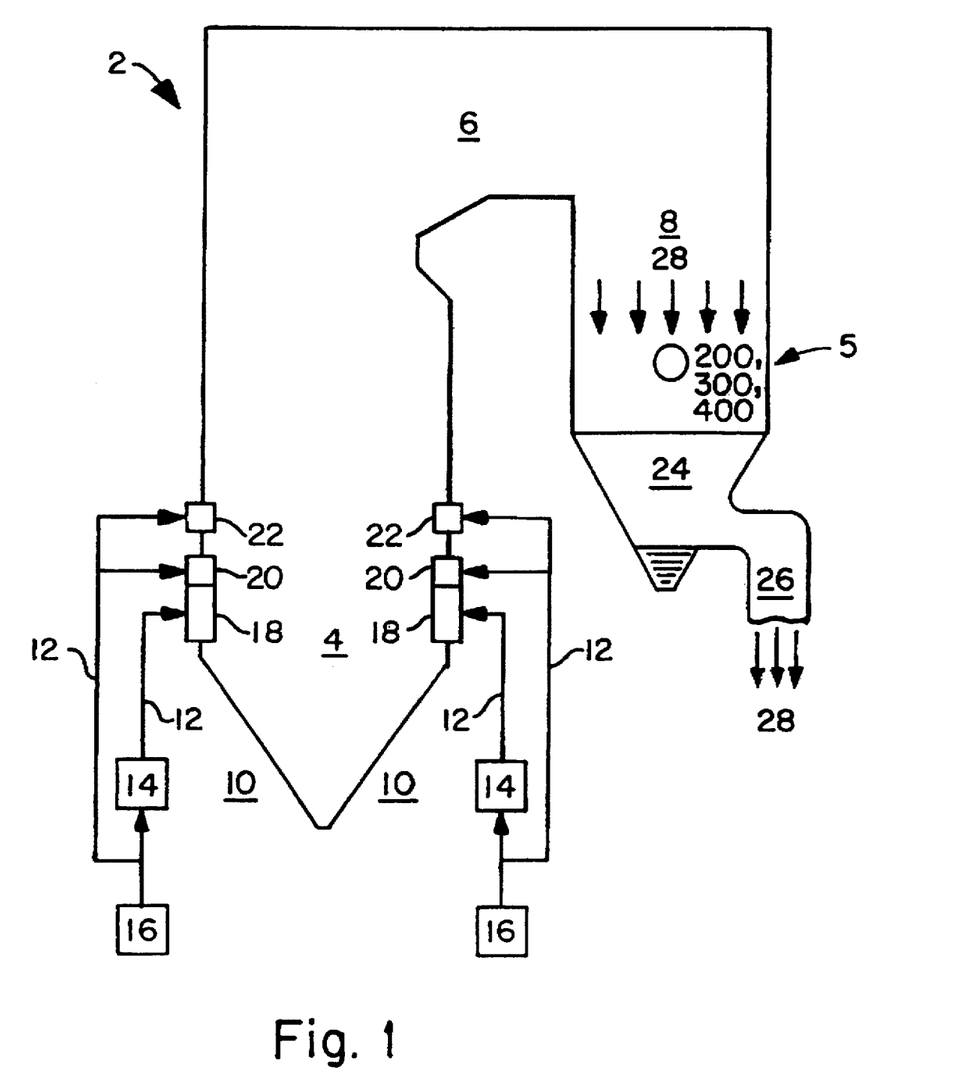
FIG. 1 is a diagrammatic representation in the nature of a vertical sectional view of a pulverized coal-fired steam generator embodying a furnace, a horizontal pass, a backpass, an economizer ash hopper and a gas duct to air heater, all in cooperation with a fuel and air supply means, with which the system of the present invention is capable of being utilized for purposes of measuring the Carbon content in the fly ash being produced therewithin.

Referring now to FIG. 1, depicted therein is a pulverized coal-fired steam generator, generally designated by reference numeral 2. Inasmuch as the nature of the construction and mode of operation of pulverized coal-fired steam generators are well known to those skilled in the art, it is not deemed necessary to set forth a detailed description of the pulverized coal-fired steam generator 2. Rather, for purposes of obtaining an understanding of a pulverized coal-fired steam generator it is deemed to be sufficient that there be presented herein merely a description of the nature of the components of the pulverized coal-fired steam generator, that are necessary for one to obtain an understanding of the subject matter of the present invention. For a more detailed description of the nature of the construction and the mode of operation of a pulverized coal-fired steam generator one may have reference to U.S. Pat. No. 4,719,587, which issued on Jan. 12, 1987 to F. J. Berte and which is assigned to the same assignee as the present U.S. patent application.

Figure 5:
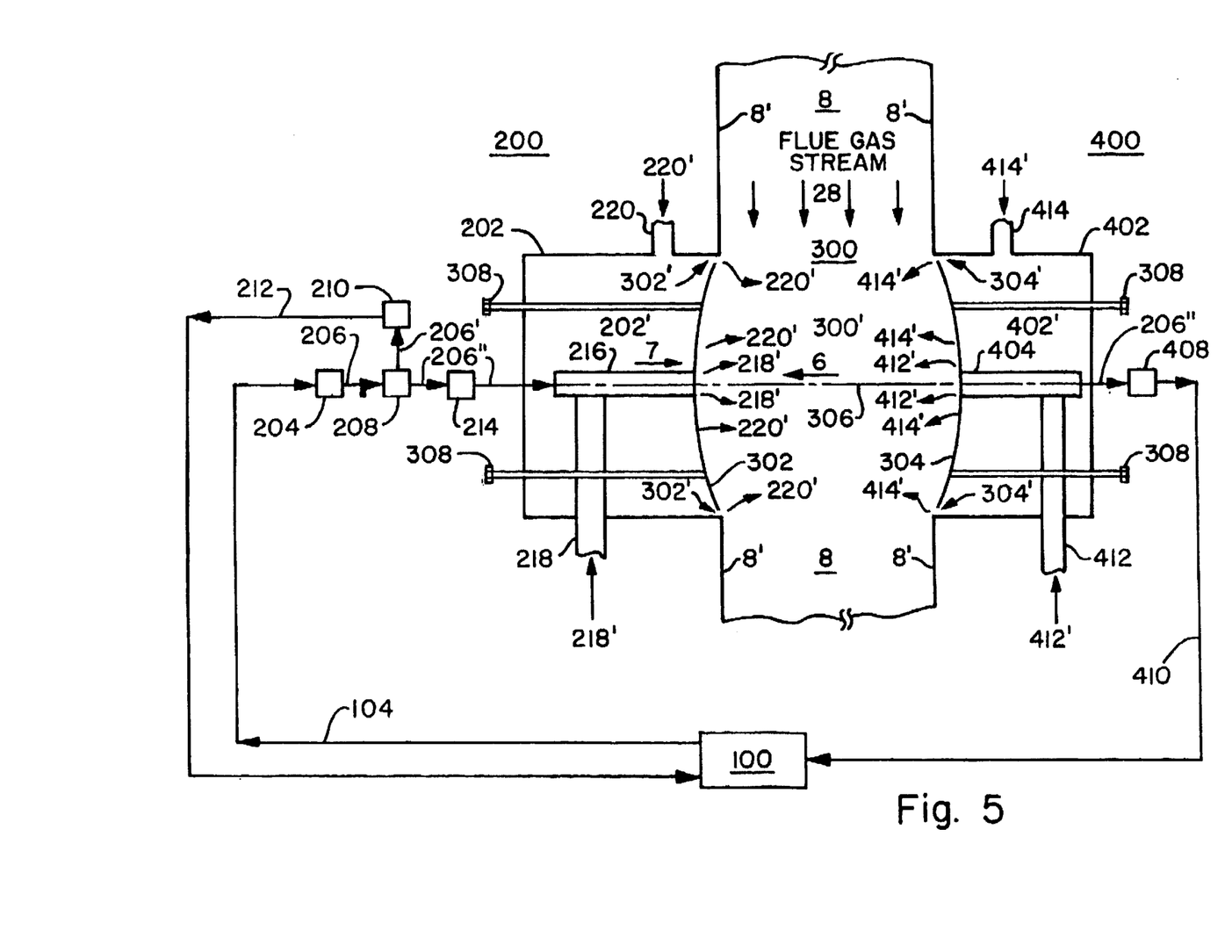
FIG. 5 is a schematic representation of the transmitting section and the cavity section and the receiving section of the resonant cavity of FIG. 2 constructed in accordance with the present invention.

Referring further to FIG. 1 the pulverized coal-fired steam generator 2 includes a main burner zone, generally designated by reference numeral 4. It is within the main burner zone 4 of the pulverized coal-fired steam generator 2 that, in a manner well known to those skilled in the art, combustion of pulverized coal and air is initiated. The hot gases that are produced from this combustion contain fly ash due to the entrainment therewith of unburned pulverized coal. These gases rise upwardly within the steam generator and give up heat to the fluid passing through the steam generator tubes (not shown for clarity of illustration) which in a conventional manner line all four walls of the steam generator 2. Then the hot combustion gases exit the steam generator 2 through the horizontal pass, generally designated by reference numeral 6. The horizontal pass 6 in turn leads to the rear gas pass 8 which in a manner similar to the steam generator 2 is enclosed by wall tubes 8' as seen in FIG. 5. Both the horizontal pass 6 and the rear pass 8 commonly contain other heat exchange surfaces (not shown for clarity) for generating and super heating steam in a manner well known to those skilled in the art. Thereafter, the steam commonly is made to flow to a turbine (not shown), which forms one component of a turbine/generator set (not shown). The steam provides the motive power to drive the turbine which thence drives the generator, which in known fashion is cooperatively associated with the turbine such that electricity is produced from the generator. After the hot combustion gases, now generally referred to as flue gases 28, have made their way through the rear pass 8 they enter first the economizer ash hopper 24, at the bottom of which boiler fly ash is collected, and secondly the gas duct to air heater 26 and thence to further processing.

Referring further to FIG. 1 there is also depicted a schematic representation of a means, generally designated by the numeral 10, for supplying pulverized coal and air to the steam generator 2. Said pulverized coal and air supply means 10 consists of various ducts 12 so designed and constructed as to transport pulverized coal and air, separately or if need be in combination, from a pulverized coal source 14 and an air source 16 to a main windbox 18 which includes a set of close coupled overfire air (CCOFA) compartments 20 and a set of separated overfire air (SOFA) compartments 22 in accordance with the illustration in FIG. 1 of steam generator 2, thence to the steam generator 2 so as to support the aforesaid combustion. For a more detailed description of the nature of construction and the mode of operation of the pulverized coal and air supply means one may have reference to U.S. Pat. No. 5,315,939, which issued on May 31, 1994 to M. Rini et al. and which is assigned to the same assignee as the present patent application.

Figure 2:
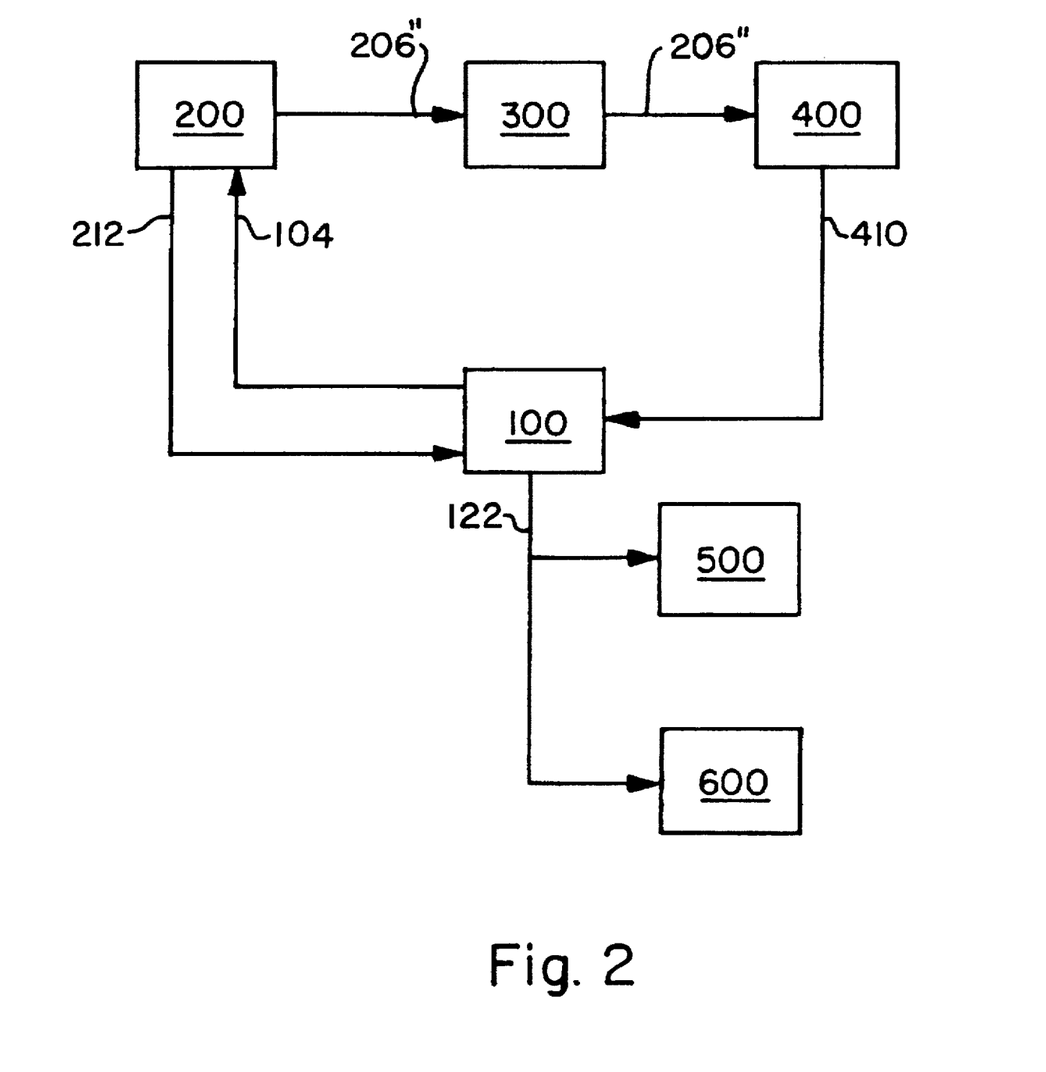
FIG. 2 is a schematic representation depicting the resonant cavity, which is employed in the system of the present invention, as consisting in accordance with the present invention of an intelligence section, a transmitting section, a cavity section and a receiving section in communication with a monitor and a boiler control system.

Referring now to FIG. 2 depicted therein is a generalized schematic diagram of the resonant cavity employed in the system of the present invention which, as illustrated, comprises an intelligence section 100, a transmitting section 200, a cavity section 300, a receiving section 400, a monitor 500, and a boiler control system 600 and their interconnecting signal paths 104, 122, 206", 212, 410. It can be seen from FIG. 2 that the intelligence section 100 is in communication, through the use of conventional means suitable for use for such purposes, with the transmitting section 200 and the receiving section 400. It is further to be understood that the cavity section 300 similarly is in communication with the transmitting section 200 and the receiving section 400. Said intelligence section 100 is suitably designed so as to be operative to provide as output therefrom an electrical drive signal 104 which acts as input to the transmitting section 200. It is also to be understood that the transmitting section 200 is suitably designed so as to be operative to provide as output both a reference electrical signal 212 which acts as one input to the intelligence section 100 and a signal 206" of electromagnetic radiation which acts as input to the cavity section 300.

Continuing with further reference to FIG. 2, it is to be understood therefrom that the cavity section 300 receives as input the signal 206" originating from the transmitting section 200 and is designed to be operative to provide as output the same signal 206" of electromagnetic radiation which then acts as input to the receiving section 400. It is also to be understood therefrom that the receiving section 400, which receives as input the signal 206" delivered from the cavity section 300, is designed to be operative to provide as output an electrical cavity signal 410 which is designed to be supplied as one input to the intelligence section 100.

With further reference to FIG. 2, it will also be understood with reference thereto that the intelligence section 100 also is designed to be operative to provide as output the signal 122, which is designed so as to be representative of the percent by mass of Carbon in the fly ash and which may be supplied as an input, such as to a monitor 500 or to an advanced boiler control system 600 or both in order that corrective action may be initiated if such is required.

Figure 3:
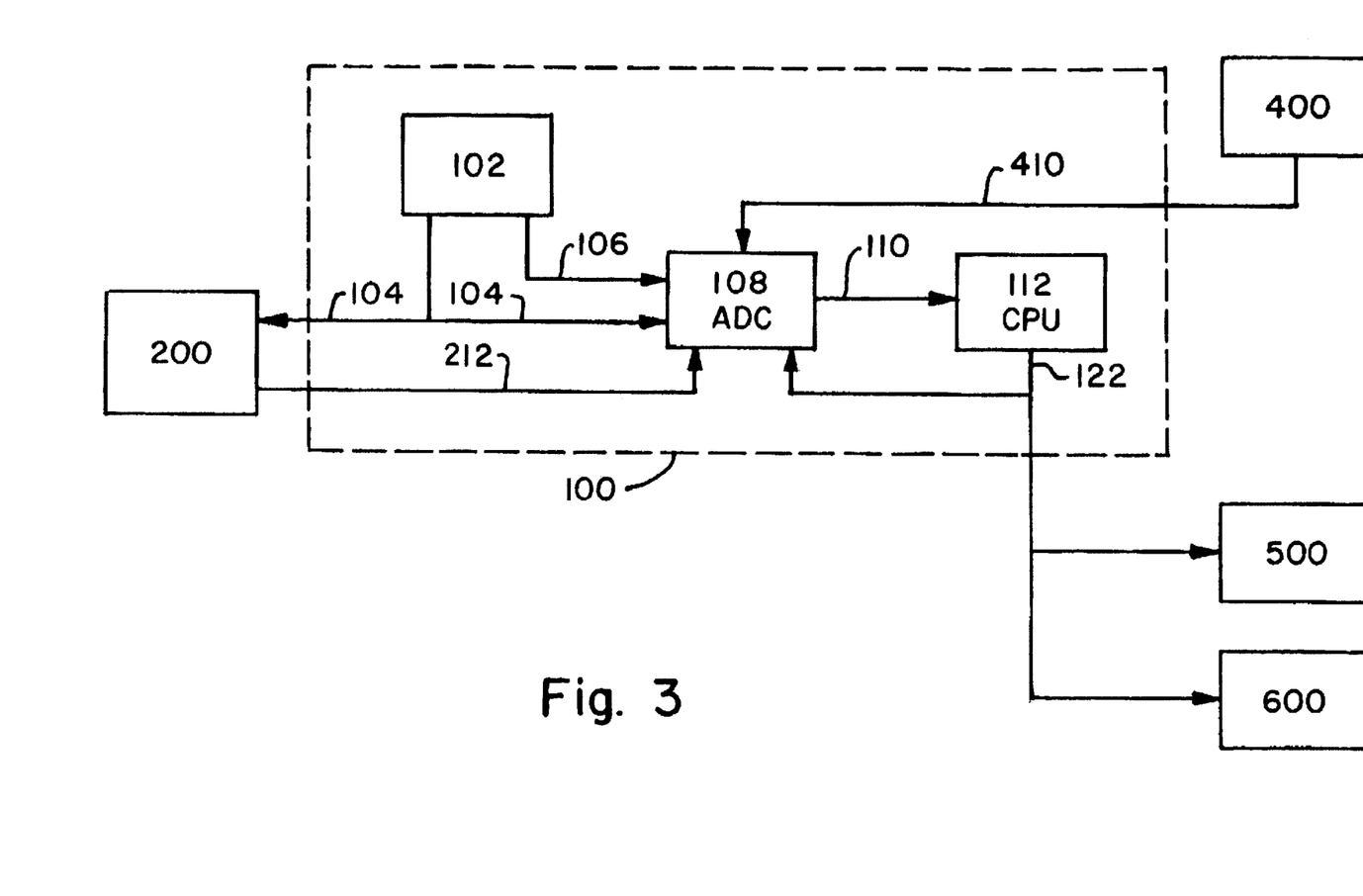
FIG. 3 is a schematic representation of the intelligence section of FIG. 2, which is illustrated therein as consisting in accordance with the present invention of a signal generator, an analog-to-digital converter and a central processing unit.

Referring now to FIG. 3, therein depicted is a schematic diagram in greater detail of the intelligence section 100. In accordance with the illustration thereof in FIG. 3, the intelligence section 100 includes the component parts 102, 108, 112 and their interconnecting signal paths 104, 106, 110, 122. More specifically, the intelligence section 100 includes a signal generator 102, an analog-to-digital converter 108 and a central processing unit 112, all of which may comprise conventional devices that are suitable for use for the purpose set forth herein.

It is to be understood from FIG. 3 that the signal generator 102 is designed to be operative to provide as output an electrical drive signal 104, described herein in more detail later, which is designed to be operative as input both to the transmitting section 200 and to the analog-to-digital converter 108. The signal generator 102 further is designed to be operative to provide as output a trigger signal 106, described herein in more detail later, which is designed to be operative as one input to the analog-to-digital converter 108.

Continuing with further reference to FIG. 3, it is to be understood therefrom that the analog-to-digital converter 108 receives as input the signals 104, 106 originating from the signal generator 102. Said analog-to-digital converter 108 further receives as input the signals 212, 410, described hereinafter, originating respectively from the transmitting section 200 and the receiving section 400. Finally, the analog-to-digital converter 108 also receives as input a command signal 122, more fully described below, which originates from the central processing unit 112. The analog-to-digital converter 108 is designed to be operative to provide as output, based upon the various inputs received thereby, a data signal 110 which, in a sequential fashion, is representative of the digitized form of the drive signal 104 or the reference signal 212 or the cavity signal 410 and which then is designed to be operative as an input to the central processing unit 112. The operation of the analog-to-digital converter 108 will be more fully described below.

With further reference to FIG. 3, it is to be understood therefrom that the central processing unit 112 receives as input the data signal 110 originating from the analog-to-digital converter 108. The central processing unit 112 contains therein data processing capabilities, described more fully hereinafter and shown schematically in FIG. 4, as well as the requisite memory for operation of the aforementioned data processing capabilities. The central processing unit 112 is designed to be operative to provide as output, based upon the input received thereby, and as a result of the operation of the data processing capabilities thereof, a command signal 122 representative of the percent of Carbon in the fly ash present within a prescribed volume, i.e., within the inspection volume 300' of FIG. 5. Said command signal 122 then preferably is supplied as input to either a monitor 500 or a boiler control system 600 or both as well as a feedback signal to the analog-to-digital converter 108. The operation of the central processing unit 112 will be more fully described below.

Figure 6:
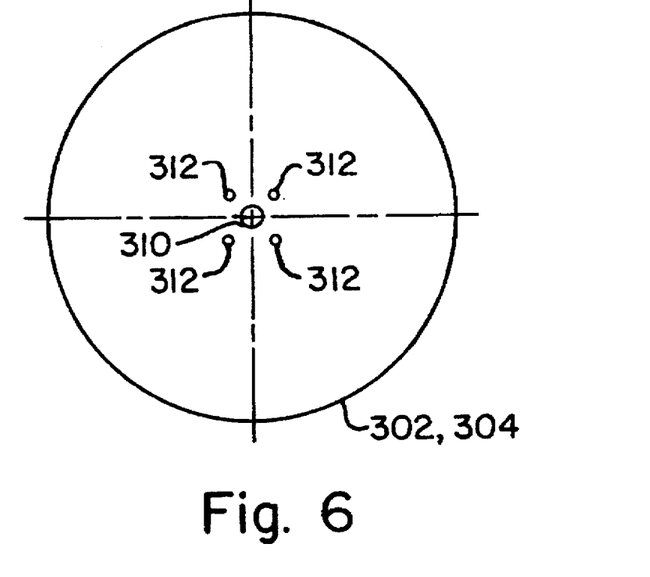
FIG. 6 is a schematic representation in the nature of a vertical sectional view of the reflecting surface of the mirrors employed in the cavity section of the resonant cavity of FIG. 2 constructed in accordance with the present invention.
Figure 7:
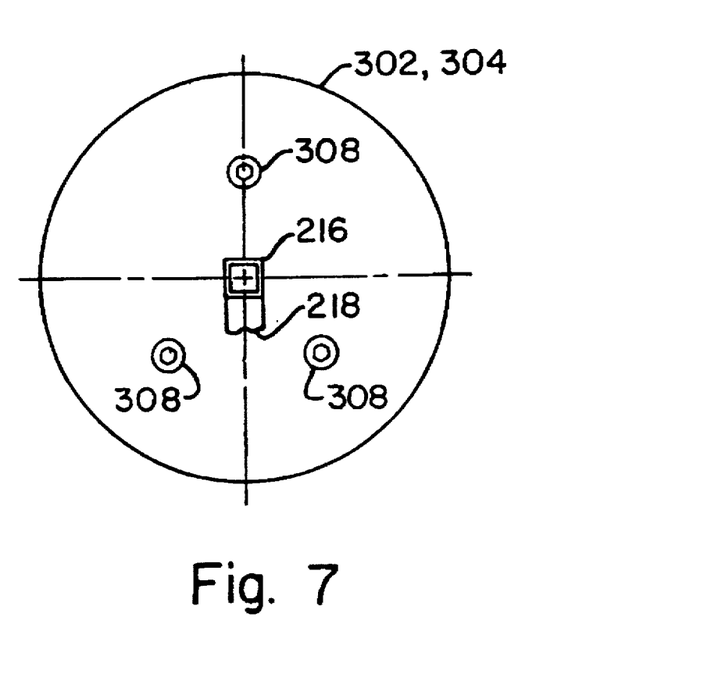
FIG. 7 is a schematic representation in the nature of a vertical sectional view of the nonreflecting surface of the mirrors employed in the cavity section of the resonant cavity of FIG. 2 constructed in accordance with the present invention.

Before providing herein a more detailed explanation of the analog-to-digital converter 108 and the central processing unit 112, it would be advantageous, in order to more fully understand the nature of the data input thereto, to first explain the operation of the cavity section 300 and its attendant components which encompass the transmitting section 200 and the receiving section 400. Therefore, reference is now made to FIG. 5 which is a view of the backpass 8 in the direction of arrow 5 in FIG. 1. Therein depicted is a schematic diagram showing in greater detail the arrangement of the transmitting section 200, the cavity section 300 and the receiving section 400 and their component parts. Said transmitting section 200 includes a pressure boundary 202, an oscillator 204, a signal coupler 208, a reference detector 210, a signal isolator 214 and a waveguide 216. The transmitting section 200 as depicted in FIG. 5 further includes a first air purge 218 and a second air purge 220. Said cavity section 300 is comprised of a first concave spherical mirror 302, a second concave spherical mirror 304, a common optical axis 306, a plurality of alignment screws 308, an inspection volume 300', a first annular ring 302' and a second annular ring 304'. Referring momentarily to FIG. 6, which is a view in the direction of arrow 6 in FIG. 5 and is typical of both concave spherical mirrors 302, 304, it can be seen therefrom that the first and second concave spherical mirrors 302, 304 each contain a pattern of circular holes that are drilled therethrough that consist of a central hole 310, so located as to be on the optical axis 306, which is common both to the first concave spherical mirror 302 and the second concave spherical mirror 304 and an array of planetary holes 312 symmetrically located about the central hole 310. In FIG. 7, which is a view in the direction of arrow 7 in FIG. 5 and is typical of both concave spherical mirrors 302, 304, it will be understood therefrom that the first and second concave spherical mirrors 302, 304 have attached to their nonreflecting sides a plurality of screws 308 symmetrically located about the center of the mirrors 302, 304 for the purpose of aligning said mirrors 302, 304 along the common optical axis 306. Returning now to FIG. 5 it will be understood therefrom that the receiving section 400 includes a pressure boundary 402, a waveguide 404 and a signal detector 408. The receiving section 400 further includes a first air purge 412 and a second air purge 414.

Continuing with reference to FIG. 5, it will be understood therefrom that the oscillator 204 receives as input the electrical drive signal 104 originating from the intelligence section 100 and which has been described above. The oscillator 204 typically may take the form of a free running biased tuned microwave oscillator, the nature of the construction and the mode of operation of which is known and understood by those skilled in the art. As a consequence of the input received thereby, the oscillator 204 generates as output a constant amplitude, sinusoidal signal 206 of electromagnetic radiation which repeatedly sweeps through a certain frequency span, $\Delta f$. The oscillator output signal 206 is supplied in known fashion to the signal coupler 208. Again in known fashion, a small fraction 206' of the oscillator output signal 206 is diverted by the signal coupler 208 to the reference detector 210, to be described hereinafter, and the remainder 206" of the oscillator output signal 206 is supplied to the waveguide 216 via the signal isolator 214. Typically the signal isolator 214 may take the form of a waveguide section filled with a ferrite material so aligned that in combination with the magnetic field of a permanent magnet, electromagnetic radiation can propagate in one direction only. The purpose of the signal isolator 214 is to prevent signal return from the cavity section 300. Since reflected energy is sharply attenuated by the signal isolator 214 it helps ensure the frequency and amplitude stability of the oscillator 204.

Returning to a consideration of the reference detector 210 depicted in FIG. 5, it will be understood that the detector 210 is designed to receive as input the signal 206' which is delivered from the signal coupler 208 in the form of electromagnetic radiation and whose power is a small fraction of the oscillator signal 206 power. The reference detector 210 typically may take the form of a full wave rectifier which may or may not be followed by a peak detector. The reference detector 210 is operative upon the input signal 206' in a known manner in order to thereby generate as output a reference signal 212 in the nature of a DC voltage proportional to the power of the input signal 206' that is supplied to the reference detector 210.

Continuing further with the description of the transmitting section 200 it is to be understood that the signal 206" in the form of electromagnetic radiation is supplied as an input to the waveguide 216 which, in accordance with the best mode embodiment of the invention, is rigidly fixed to the non-reflecting side of the first concave spherical mirror 302 so as to be aligned along the common optical axis 306. The waveguide 216 in turn is designed so as to be operative to deliver the signal 206" to the cavity section 300 via the central hole 310 which is illustrated in FIG. 6. It is further to be understood that the waveguide 216, in accordance with the best mode embodiment of the invention, is preferably equipped with a first air purge 218. The air purge 218 is designed to be operative so as to direct an external source of pressurized air 218' into and along the waveguide 216 through to the cavity section 300 via the central hole 310 depicted in FIG. 6. Such purging activity helps prevent fouling of the mirror 302 and the waveguide 216 which might otherwise occur due to fly ash buildup.

It is further to be understood that the transmitting section 200 includes a pressure boundary 202. The pressure boundary 202 may or may not enclose the oscillator 204, the signal coupler 208, the reference detector 210 and the signal isolator 214. The pressure boundary 202 coupled with the first spherical mirror 302 and an annular ring 302' concentric with the mirror 302 is intended to define a volume 202' which undergoes purging similar to that which has been described above. Such purging directs an external source of pressurized air 220' into the aforesaid volume 202' through to the cavity section 300 via the annular ring 302' and the planetary holes 312 shown in FIG. 6. Said purging activity helps prevent fouling of the mirror 302 which might otherwise occur due to fly ash buildup.

Figure 9:
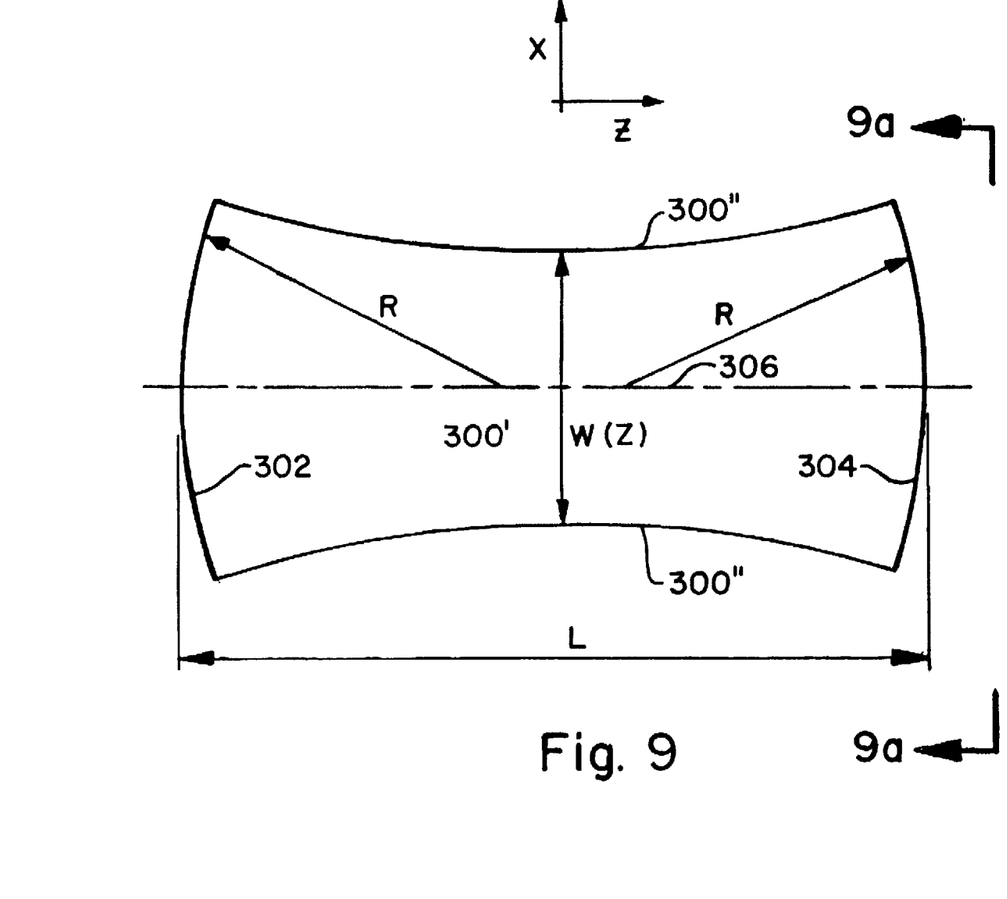
FIG. 9 is a schematic representation of the essential dimensions of the resonant cavity that is employed in the system of the present invention.

Referring again to FIG. 5 reference will now be made to the cavity section 300. The cavity section 300 includes the first concave spherical mirror 302 and the second concave spherical mirror 304, each aligned along the common optical axis 306 and so oriented that their reflective sides face one another. For purposes of the description thereof the cavity section 300 further is considered to encompass the approximately cylindrical inspection volume 300' subtended by the concave spherical mirrors 302, 304, as the latter are separated by a fixed distance, L, along the common optical axis 306, and an imaginary boundary 300" (shown in FIG. 9) delimited by the spot size, w(z), to be described hereinafter. It is through and across this inspection volume 300' that the flue gas stream 28 is made to flow, carrying with it boiler fly ash.

As described hereinabove, the sinusoidal signal 206" of electromagnetic radiation is supplied to the cavity section 300 from the transmitting section 200 via the waveguide 216. The signal 206" enters the inspection volume 300' from the center hole 310 depicted in FIG. 6. The signal 206" propagates through the inspection volume 300' to the second concave spherical mirror 304 and is reflected back to the first concave spherical mirror 302 to be reflected once again back to the second concave spherical mirror 304. To this end the signal 206" is reflected back and forth between the two spherical mirrors 302, 304 numerous times. The resulting steady state signal 206" is captured by the second concave spherical mirror 304 at the center hole 310 shown in FIG. 6. The signal 206" is then delivered by way of the waveguide 404 to the signal detector 408. The waveguide 404, in accordance with the best mode embodiment of the invention, preferably is rigidly fixed to the non-reflecting side of the second concave spherical mirror 304 so as to be aligned along the common optical axis 306. The signal detector 408 receives as input, from the cavity section 300, the signal 206" that is in the form of electromagnetic radiation. Typically the signal detector 408 may take the form of a full wave rectifier which may or may not be followed by a peak detector. The signal detector 408 is operative upon the input signal 206" in known fashion to provide as an output therefrom, a cavity signal 410 which is in the nature of a DC voltage that is proportional to the power of the input signal 206" to the signal detector 408. The cavity signal 410 then functions as one input to the intelligence section 100.

It is further seen from reference to FIG. 5 that the receiving section 400 includes a pressure boundary 402. The pressure boundary 402 may or may not enclose the signal detector 408. The pressure boundary 402 coupled with the second concave spherical mirror 304 and an annular ring 304', concentric with the second concave spherical mirror 304, define a volume 402' which, preferably in accordance with the best mode embodiment of the invention, undergoes purging from an external source of pressurized air 414' similar to that which has been described hereinabove, with respect to the transmitting section 200. Furthermore, the waveguide 404 that directs the captured signal 206" to the signal detector 408 also, preferably in accordance with the best mode embodiment of the invention, undergoes a purging process from an external source of pressurized air 412' similar to that which has been described hereinabove, with respect to the transmitting section 200. Such purging helps prevent fouling of the mirror 304 and waveguide 404 as a result of fly ash buildup, which might otherwise occur.

In referring to the manner in which the component elements of the resonant cavity are affixed to the rear gas pass 8 of the boiler complex, attention is directed in this regard to the pressure boundaries 202, 402 that are depicted in FIG. 5. The pressure boundaries 202, 402 are rigidly fixed by any type of conventional means suitable for use for such purpose, to the opposing walls 8' of the rear gas pass 8 at nearly the same elevation. The first and second concave spherical mirrors 302, 304 of the cavity section 300 are in turn mounted to the pressure boundaries 202, 402 via the alignment screws 308 so as to be capable of mutual alignment along the common optical axis 306 by way of the alignment screws 308. It should be noted that the first and second concave spherical mirrors 302, 304 are not affixed directly to the walls 8' of the rear gas pass 8.

Figure 4:
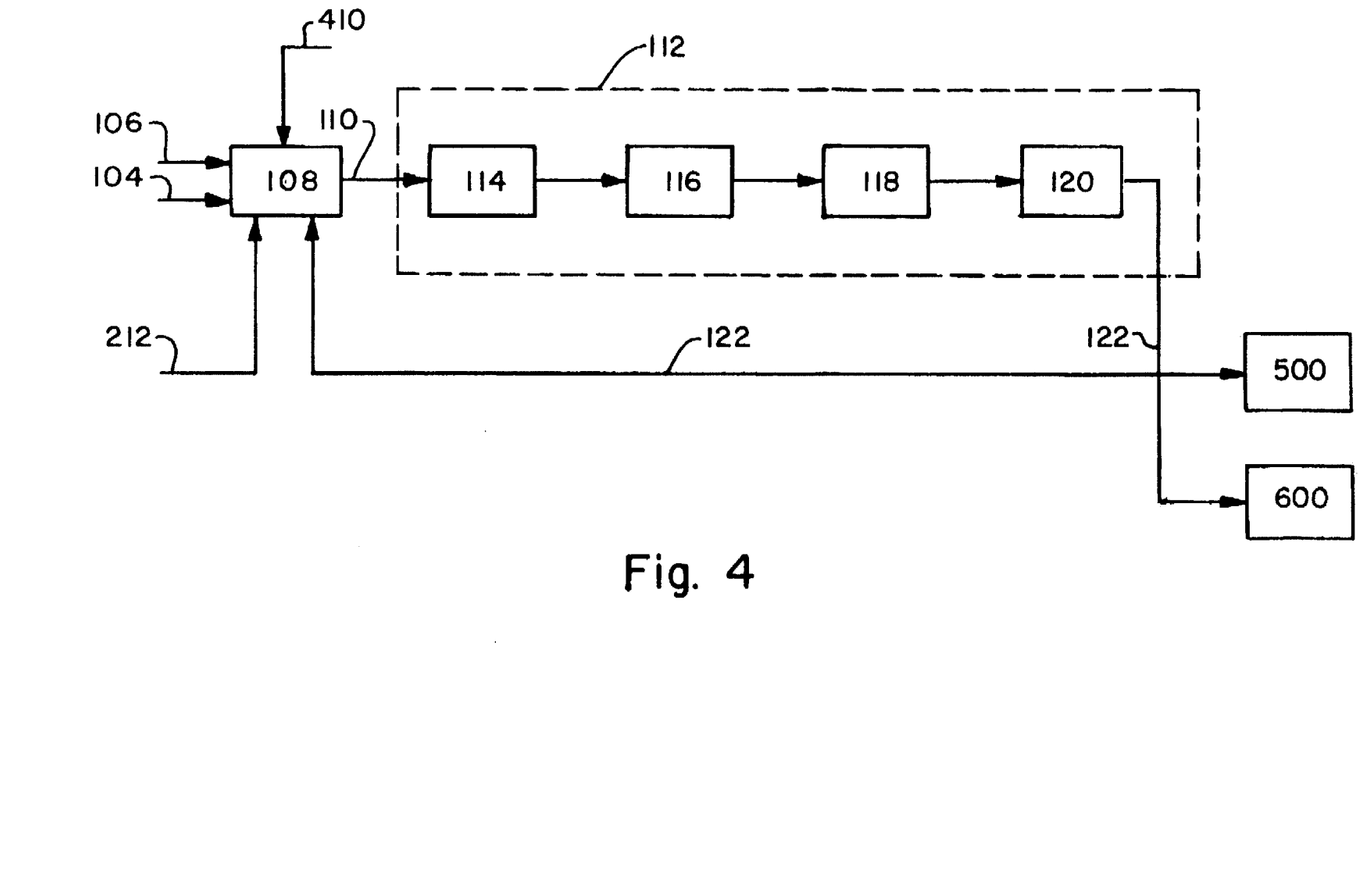
FIG. 4 is a schematic representation of the central processing unit of FIG. 3 depicted as being comprised in accordance with the present invention of several data processing steps.

Returning now to a description of the manner in which the analog-to-digital converter (ADC) 108 and the central processing unit (CPU) 112 acquire and process data, reference is had for this purpose to FIG. 4. Therein depicted is a schematic diagram illustrating the analog-to-digital converter 108 as being in communication with the central processing unit 112 via the data signal 110 and the command signal 122. FIG. 4 also shows a schematic representation in greater detail of the central processing unit 112. In accordance with the illustration thereof in FIG. 4, the central processing unit includes a sequence of data processing steps 114, 116, 118, 120.

The purpose of the analog-to-digital converter 108 is to repetitively sample certain analog data, digitize this data and deliver the digitized data to the central processing unit 112. As has been described hereinabove, the analog-to-digital converter 108 receives a drive signal 104 as input thereto. The drive signal 104 is a biased, periodic ramp voltage which also activates the oscillator 204 causing the oscillator to sweep through a predetermined frequency span, Δf. Furthermore, the analog-to-digital converter 108 receives a trigger signal 106 as input. The trigger signal 106 is a very short duration voltage pulse generated at the moment the drive signal 104 begins to ramp up. The trigger signal 106 is used to synchronize the generation of successive ramps with the sampling of data by the analog-to-digital converter 108. The analog-to-digital converter 108 also receives as input the reference signal 212 which is a DC voltage proportional to the power of the input signal 206' to the reference detector 210. The analog-to-digital converter 108 further accepts as input the cavity signal 410 which is a DC voltage proportional to the power of the input signal 206" to the cavity detector 408. The analog-to-digital converter 108 finally receives as input the command signal 122 which originates from the central processing unit 112, as feedback and which causes the analog-to-digital converter 108 to sample the next data set. The analog-to-digital converter 108 is operative to provide as an output, based upon the input received thereby, a data signal 110 which, in a sequential fashion, is representative of the digitized form of the drive signal 104 or the reference signal 212 or the cavity signal 410 and which is supplied as an input to the central processing unit 112.

Figure 8:
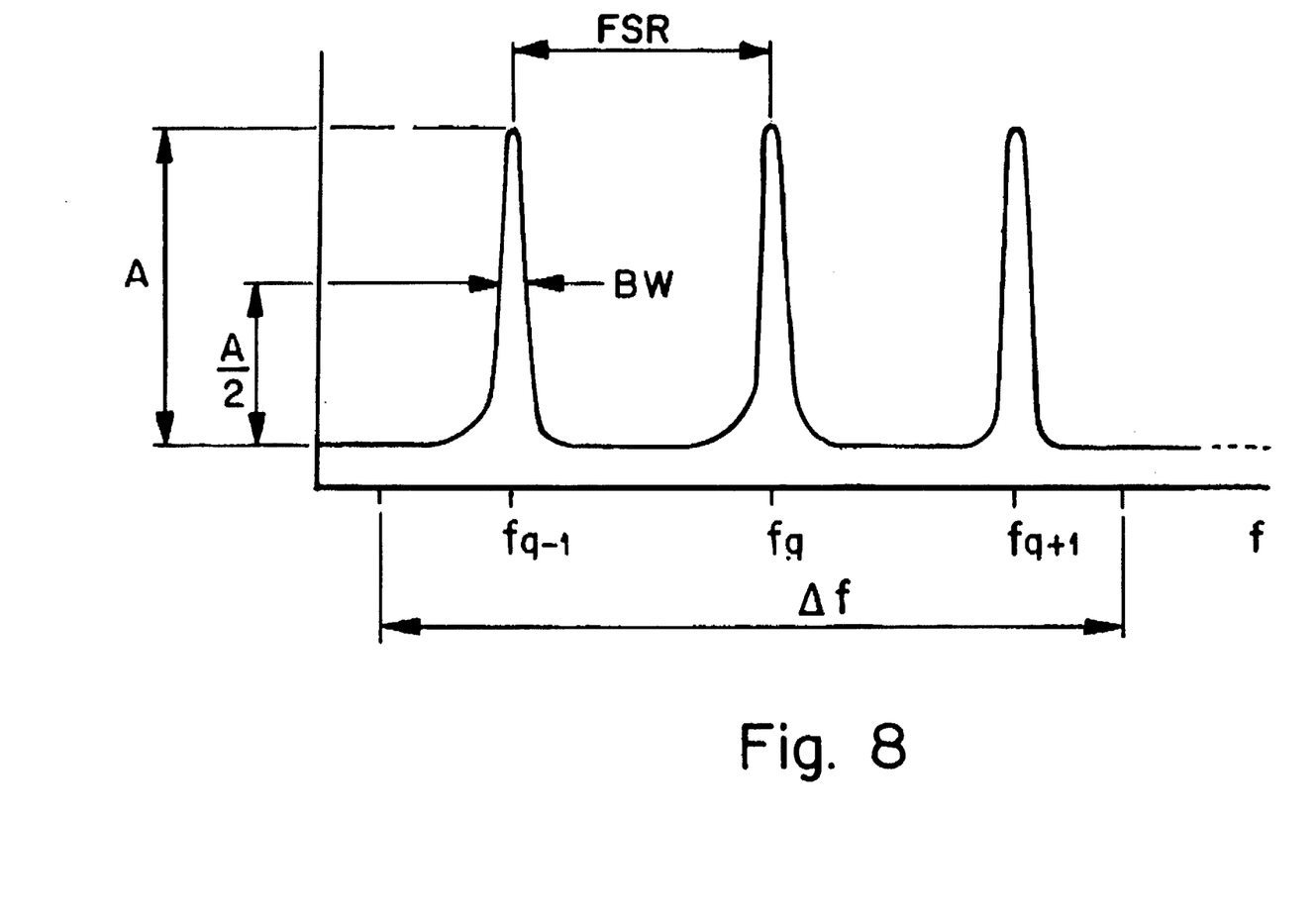
FIG. 8 is a graphical representation of resonance profiles typical of resonant cavities.

As the transmitted signal 206" is swept through its frequency span, Δf, and reflected back and forth between the mirrors 302, 304, one or more cavity resonances may be excited. The resonances are typified by repetitive, sharp peaks in the power of the transmitted signal 206" detected at the receiver 408. A resonance profile representative of resonant cavities is shown in FIG. 8. Such a data profile is presented to the central processing unit 112, via the data signal(s) 110.

The purpose of the central processing unit 112 is to accept the sequential data signal(s) 110, which have been described above, and to process the signal(s) 110 so as to characterize any resonances excited within the cavity 300. The central processing unit 112, as will be explained below, is operative such that, when resonances are excited within the cavity 300, four key cavity parameters may be determined: first, the resonant frequencies, $f_q$, themselves; second, the corresponding resonant amplitudes, $A_q$; thirdly, the corresponding full width at half maximum (FWHM) frequency differences, $BW_q$; and fourthly the free spectral range, FSR. A representative showing of these cavity parameters can be found depicted in FIG. 8.

For a given frequency span, Δf, the first step 114 in the data processing is that of data acquisition and memory. Within this step 114 the drive signal 104, the reference signal 212 and the cavity signal 410 are received sequentially and placed in memory. This data field is averaged over a predetermined number of sweeps, giving an average resonance profile. The second step 116 in the data processing is that of resonance characterization. Within this step 116 the two largest resonant peaks are found from the average resonance profile. At these two frequencies ($f_1$ and $f_2$) the corresponding amplitudes ($A_1$ and $A_2$) are determined along with the corresponding full width at half maximum frequency differences ($BW_1$ and $BW_2$) as well as the Free Spectral Range (FSR). The third step 118 in the data processing is that of calibration. The values for $A_1$ and $A_2$ are compared against a previously established calibration curve. This curve gives amplitude, A, as a function of Carbon content to yield the Carbon content of the fly ash found within the inspection volume 300' expressed in milligrams of Carbon per cubic meter. Further, the values for $BW_1$ and $BW_2$ are also compared against a previously established calibration curve. This curve gives the FWHM frequency difference, BW, as a function of Carbon content to again yield the Carbon content of the fly ash found within the inspection volume 300' expressed in milligrams of Carbon per cubic meter. This yields four values of the Carbon content of the fly ash from which an appropriate value is chosen. Next the Free Spectral Range, FSR, is compared against a previously established calibration curve of Free Spectral Range as a function of fly ash concentration to yield the fly ash concentration within the inspection volume 300' measured in milligrams of total ash per cubic meter. The Carbon content of the fly ash is then ratioed against the fly ash concentration within the inspection volume 300' to give a load insensitive value for the percent of Carbon in the fly ash expressed in milligrams of Carbon per milligram of fly ash.

The calibration curves mentioned above are derived in a two step process. First, laboratory measurements are taken to separately determine amplitude, A, and FWHM frequency difference, BW, as functions of Carbon content. A relationship is also derived for the Free Spectral Range, FSR, as a function of fly ash concentration. Secondly, at the time of installation of the resonant cavity, field testing is performed under various boiler loads to optimize the calibration curves.

The final step 120 of the data processing is that of data comparison. The value of the Carbon content of the fly ash is compared against previous values and an appropriate value chosen. When the appropriate value for the percent of Carbon in fly ash is established a command signal 122 is fedback to the analog-to-digital converter 108 which causes the analog-to-digital 108 to sample the next sequence of data. The command signal 122 also is supplied as input to a monitor 500 or a boiler control system 600 or both in order that corrective action may be implemented when such is required.

Figure 9A:
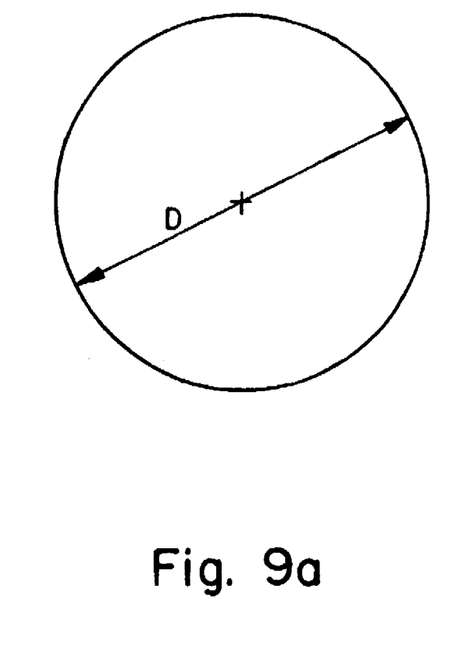
FIG. 9a is a sectional view of the resonant cavity of FIG. 2 showing the mirror diameter, taken substantially along the line 9a—9a in FIG. 9, constructed in accordance with the present invention.

By way of exemplification but not limitation, reference is now made to the criteria governing the selection of the cavity dimensions. In so doing attention is drawn to FIGS. 9 and 9a wherein depicted are the essential cavity dimensions of length, L; radius of curvature, RM, of the mirrors 302, 304; beam spot size, w(z); mirror diameter, D; and an imaginary boundary 300" enclosing the inspection volume 300'. The width, L, of the cavity is governed by the length of the rear gas pass 8. However, the ratio of L/RM is chosen based upon consideration of well established practice so as to ensure resonant cavity stability. With this ratio and a first estimate of frequency, f, the minimum beam spot size, w(0), can be calculated. With this spot size, the diameter of the mirrors, D, can be found such as by utilizing, for example, the "rule of thumb" that D/w(0) is approximately equal to 4. This value for mirror diameter, D, is compared to a predetermined mirror diameter and another value chosen for frequency, f, and/or D/w(L/2) until a desired mirror diameter is selected.

It will be appreciated that modifications may be made to our invention by those skilled in the art. We, therefore, intend by the appended claims to cover all other modifications which fall within the true spirit and scope of our invention.

What is claimed is:

1. In a solid fuel-fired steam generator a system for measuring in-situ and in real time the Carbon content of the flue gas entrained fly ash that is produced from the combustion occurring within the solid fuel-fired steam generator comprising:

a. means defining a flue gas flow path through the solid fuel-fired steam generator;
   b. an inspection volume area located within the solid fuel-fired steam generator along the length of the flue gas flow path therethrough, said inspection volume area including a first spherical mirror and a second spherical mirror separated one from another by a fixed distance and so arranged as to be aligned along a common optical axis with their respective reflecting sides facing one another, and an imaginary boundary delimited by a spot size;
   c. resonant cavity means including data processing means, signal transmission means, signal reception means including a first waveguide, and repetitive signal reflection means, said data processing means being connected in signal communication with said signal transmission means and in signal communication with said signal reception means, said data processing means selectively being further capable of being connected in signal communication with a signal display means and a boiler control means, said repetitive signal reflection means being connected in signal communication with said signal transmission and in signal communication with said signal reception means, said repetitive signal reflection means including an inspection volume means; and
   d. means supporting said resonant cavity means in said inspection volume area such that said resonant cavity is operative for measuring the Carbon content of the flue gas entrained fly ash in the course of the passage of the flue gas entrained fly ash through said inspection volume area.

2. In a solid fuel-fired steam generator a system as set forth in claim 1, wherein said first spherical mirror and said second spherical mirror each having a center hole drilled therethrough and such as to be located on the common optical axis in order thereby to allow access of the oscillator signal to the inspection volume means, to allow capture of the oscillator signal from the inspection volume means, and further to allow air purging of said first waveguide to prevent fouling of said first waveguide.

3. In a solid fuel-fired steam generator a system as set forth in claim 2 wherein said first spherical mirror and said second spherical mirror each have a plurality of holes drilled therethrough and such as to be located symmetric the common optical axis in order thereby to allow air purging of the inspection volume means to prevent fouling of said first spherical mirror and said second spherical mirror.

4. In a solid fuel-fired steam generator a system as set forth in claim 3 wherein said first spherical mirror and said second spherical mirror each being provided upon the non-reflecting side thereof with a plurality of adjusting screws located symmetric with the common optical axis in order thereby to allow for alignment of said first spherical mirror and said second spherical mirror relative to the common optical axis.

5. In a solid fuel-fired steam generator a system for measuring in-situ and in real time the carbon content of the flue gas entrained fly ash that is produced from the combustion occurring within the solid fuel-fired steam generator comprising:

a. means defining a flue gas flow path through the solid fuel-fired steam generator;
   b. an inspection volume area located within the solid fuel-fired steam generator along the length of the flue gas flow path therethrough;
   c. resonant cavity means including data processing means, signal transmission means, signal reception means and repetitive signal reflection means, said data processing means being connected in signal communication with said signal transmission means and in signal communication with said signal reception means, said data processing means selectively being further capable of being connected in signal communication with a signal display means and a boiler control means, said data processing means including a signal generator, an analog-to-digital converter and a central processing unit, said signal generator being operative to produce a drive signal operative to drive an oscillator and a trigger signal operative to effectuate signal timing and signal averaging, said analog-to-digital converter being operative to receive an input signal operative as a drive signal, an input signal operative as a trigger signal, an input signal operative as a reference signal, an input signal operative as a detected signal, an input signal operative as a command signal, said analog-to-digital converter further being operative to produce an output signal operative as a data signal, said repetitive signal reflection means being connected in signal communication with said signal transmission means and in signal communication with said signal reception means; and
   d. means supporting said resonant cavity means in said inspection volume area such that said resonant cavity means is operative for measuring in-situ and in real time the carbon content of the flue gas entrained fly ash in the course of the flue gas entrained fly ash through said inspection volume area.

6. In a solid fuel-fired steam generator a system as set forth in claim 5 wherein said central processing unit receives an input signal operative as a data signal and produces an output signal operative as a command signal.

7. In a solid fuel-fired steam generator a system for measuring in-situ and in real time the carbon content of the flue gas entrained fly ash that is produced from the combustion occurring within the solid fuel-fired steam generator comprising:

a. means defining a flue gas flow path through the solid fuel-fired generator;

b. an inspection volume area located within the solid fuel-fired steam generator along the length of the flue gas flow path therethrough;

c. resonant cavity means including data processing means, signal transmission means, signal reception means and repetitive signal reflection means, said data processing means being connected in signal communication with said signal transmission means and in signal communication with said signal reception means, said data processing means selectively being further capable of being connected in signal communication with a signal display means and a boiler control means, said signal transmission means including an oscillator, a signal coupler, a reference detector, a signal isolator, a first waveguide, a first air purge means, a second air purge means and a pressure boundary, said repetitive signal reflection means being connected in signal communication with said signal transmission means and in signal communication with said signal reception means; and d. means supporting said resonant cavity means in said inspection volume area such that said resonant cavity means is operative for measuring in-situ and in real time the carbon content of the flue gas entrained fly ash in the course of the passage of the flue gas entrained fly ash through said inspection volume area.

8. In a solid fuel-fired steam generator a system as set forth in claim 7 wherein said oscillator receives an input signal operative as a drive signal and produces an output signal operative as an oscillator signal in the form of electromagnetic radiation.

9. In a solid fuel-fired steam generator a system as set forth in claim 8 wherein said signal coupler receives the oscillator signal as an input signal thereto and produces a first output signal and a second output signal with the power of the first output signal being a small fraction of the power of the oscillator signal.

10. In a solid fuel-fired steam generator a system as set forth in claim 9 wherein said reference detector receives an input signal of electromagnetic radiation and produces an output signal operative as a reference signal in the form of a DC voltage.

11. In a solid fuel-fired steam generator a system as set forth in claim 9 wherein said signal isolator receives the oscillator signal as an input signal thereto for the purpose of preventing signal return from said resonant cavity means and produces as an output signal therefrom the oscillator signal.

12. In a solid fuel-fired steam generator a system as set forth in claim 11 wherein said waveguide receives the oscillator signal as an input signal thereto and is operative for the purpose of guiding the oscillator signal and delivering the oscillator signal to said repetitive signal reflection means.

13. In a solid fuel-fired steam generator a system for measuring in-situ and in real time the carbon content of the flue gas entrained fly ash that is produced from the combustion occurring within the solid fuel-fired steam generator comprising:

a. means defining a flue gas flow path through the solid fuel-fired steam generator;

b. an inspection volume area located within the solid fuel-fired steam generator along the length of the flue gas flow path therethrough;

c. resonant cavity means including data processing means, signal transmission means, signal reception means and repetitive signal reflection means, said data processing means being connected in signal communication with said signal transmission means and in signal communication with said signal reception means, said data processing means selectively being further capable of being connected in signal communication with a signal display means and a boiler control means, said signal reception means including a waveguide, a detector, a first air purge, a second air purge and a pressure boundary, said repetitive signal reflection means being connected in signal communication with said signal transmission means and in signal communication with said signal reception means; and d. means supporting said resonant cavity means in said inspection volume area such that said resonant cavity is operative for measuring the Carbon content of the flue gas entrained fly ash in the course of the passage of the flue gas entrained fly ash through said inspection volume area.

14. In a solid fuel-fired steam generator a system as set forth in claim 13 wherein said waveguide receives the oscillator signal as an input signal thereto and is operative for the purpose of guiding the oscillator signal and for delivering the oscillator signal to said detector.

15. In a solid fuel-fired steam generator a system as set forth in claim 14 wherein said detector receives an input signal of electromagnetic radiation and produces an output signal operative as the cavity signal embodying the form of a DC voltage.

* * * * *